United States Patent [19]

Böhagen et al.

[11] Patent Number: 5,374,647
[45] Date of Patent: Dec. 20, 1994

[54] ANTITHROMBOTIC SUBSTITUTED CYCLOALKANO (B) DIHYDROINDOLE SULPHONAMIDES

[75] Inventors: Horst Böhagen, Haan; Ulrich Müller, Wuppertal; Ulrich Rosentreter, Wuppertal; Erwin Bischoff, Wuppertal; Volker-Bernd Fiedler, Leverkusen; Elisabeth Perzborn, Wuppertal; Joachim Hütter, Leverkusen, all of Germany; Peter Norman, Cippenham, United Kingdom; Nigel J. Cuthbert, Great Missenden, United Kingdom; Hilary P. Francis, Woodley, United Kingdom; Marie G. McKenniff, Slough, United Kingdom

[73] Assignee: Bayer Aktiengesellschaft, Leverkusen, Germany

[21] Appl. No.: 42,857

[22] Filed: Apr. 5, 1993

Related U.S. Application Data

[60] Continuation of Ser. No. 786,478, Nov. 1, 1991, abandoned, which is a division of Ser. No. 678,563, Mar. 28, 1991, Pat. No. 5,096,897, which is a division of Ser. No. 599,321, Oct. 17, 1990, Pat. No. 5,039,670.

[30] Foreign Application Priority Data

Oct. 30, 1989 [GB] United Kingdom ................ 8924392

[51] Int. Cl.$^5$ .................... A61K 31/40; C07D 209/88
[52] U.S. Cl. .................................... 514/411; 548/449
[58] Field of Search ........................ 548/449; 514/411

[56] References Cited

U.S. PATENT DOCUMENTS 4,808,608 2/1989 Guindon et al. ............... 548/439
4,965,258 10/1990 Böshagen et al. ............. 548/449

Primary Examiner—Robert W. Ramsuer
Attorney, Agent, or Firm—Sprung Horn Kramer & Woods

[57] ABSTRACT

Substituted antithrombotic substituted cycloalkano[b-]dihydroindole- and -indole-sulphonamides for treatment of thromboses, thromboembolisms, ischaemias, asthma and allergies, of the formula

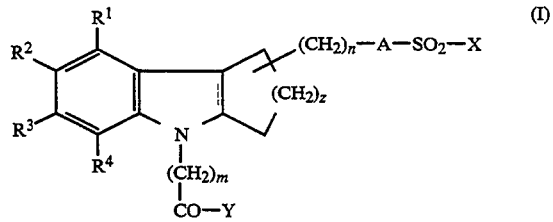

in which
$R^1$, $R^2$, $R^3$ and $R^4$ are hydrogen or other radicals,
X is aryl, alkyl or $CF_3$,
m and Z each is 1,2,3 or 4,
n is 0,1 or 2,
A is a bond or —NH—, and
Y is OH, alkoxy, aryloxy, amino or sulphonylamine,
with the proviso, that in all cases, two of the substituents $R^1$–$R^4$ are other than hydrogen in the event that m represents the number 2 and Y represents the hydroxyl group, or a salt thereof.

6 Claims, No Drawings

ANTITHROMBOTIC SUBSTITUTED CYCLOALKANO (B) DIHYDROINDOLE SULPHONAMIDES

This application is a continuation of application Ser. No. 786,478, filed Nov. 1, 1991, abandoned, which is a division of Ser. No. 678,563, filed Mar. 28, 1991, now U.S. Pat. No. 5,096,897.

The invention relates to substituted cycloalkano[b]dihydroindole- and -indole-sulphonamides, to processes for their preparation, and to their use in medicaments.

It is already known that cycloalkano[b]dihydroindole-and-indole-sulphonamides are active as inhibitors of thrombocyte aggregation [cf. DOS (German Published Specification) 3,631,824].

Substituted cycloalkano[b]dihydroindole-and-indolesulphonamnides of the general formula (I) have now been found

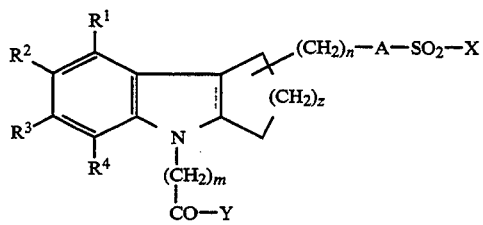

in which formula $R^1$, $R^2$, $R^3$ and $R^4$ are identical or different and
represent hydrogen, nitro, cyano, halogen, trifluoromethyl, carboxyl, hydroxyl or trifluoromethoxy, or
represent a group of the formula $—S(O)_wR^5$ where
$R^5$—represents straight-chain or branched alkyl having up to 8 carbon atoms or represents aryl which has 6 to 10 carbon atoms and which, in turn, is substituted by halogen, nitro, cyano or trifluoromethyl and
w—represents a number 0, 1 or 2, or represent straight-chain or branched alkoxy or alkoxycarbonyl, each of which has up to 10 carbon atoms, or represent benzyloxy, or
represent a group of the formula $—NR^6R^7$ where
$R^6$ and $R^7$ are identical or different and
represent hydrogen, straight-chain or branched alkyl or acyl, each of which has up to 8 carbon atoms, or
represent aryl having 6 to 10 carbon atoms, or
represent cycloalkyl having 3 to 8 carbon atoms or
represent aryl having 6 to 10 carbon atoms, or
represent straight-chain or branched alkyl or alkenyl, each of which has up to 10 carbon atoms and each of which is optionally substituted by halogen, hydroxyl, carboxyl, cyano, aryl having 6 to 10 carbon atoms, straight-chain or branched alkyl, alkoxy or alkoxycarbonyl, each of which has up to 8 carbon atoms, or by a group of the formula

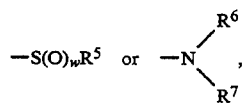

where w, $R^5$, $R^6$ and $R^7$ have the abovementioned meanings,

X—represents aryl which has 6 to 10 carbon atoms and which can optionally be up to pentasubstituted by identical or different substituents from the series comprising nitro, halogen, cyano, trifluoromethyl, trifluoromethoxy, trifluoromethylthio, hydroxyl, carboxyl, aryl or aryloxy having 6 to 10 carbon atoms, and straight-chain or branched alkoxy or alkoxycarbonyl, each of which has up to 8 carbon atoms, or by straight-chain or branched alkyl which has up to 8 carbon atoms and which, in turn, can be substituted by carboxyl, hydroxyl, alkoxycarbonyl having up to 6 carbon atoms or aryl having 6 to 10 carbon atoms, or by a group of the formula $—S(O)_wR^5$ or $—NR^6R^7$, where
w, $R^5$, $R^6$ and $R^7$ have the abovementioned meanings, or
represents a straight-chain or branched alkyl having up to 8 carbon atoms or
represents trifluoromethyl,
m—represents the number 1, 2, 3 or 4,
n—represents the number 0, 1 or 2,
z—represents the number 1, 2, 3 or 4,
A—represents a bond or the —NH group, and
Y—represents hydroxyl, alkoxy having up to 8 carbon atoms, aryloxy having 6 to 10 carbon atoms or the group $—NR^6R^7$ where
$R^6$ and $R^7$ have the abovementioned meanings, or
represents a group of the formula $—NH—SO_2—R^5$ where
$R^5$—has the abovementioned meaning,
with the proviso that, in all cases, two of the substituents $R^1$—$R^4$ are other than hydrogen in the event that m represents the number 2 and Y represents the hydroxyl group, if appropriate in an isomeric form, and salts of these compounds.

The substituted cycloalkano[b]dihydroindole- and -indolesulphonamides according to the invention have one or more asymmetric carbon atoms and can therefore exist in various stereochemical forms. It is also possible for regioisomers to occur. The individual isomers and mixtures thereof are all a subject of the invention.

The compounds according to the invention exist in stereoisomeric forms which are either like image and mirror-image (enantiomers) or not like image and mirror-image (diastereomers). The invention relates to the antipodes and to the racemic forms and to the mixtures of diastereomers. The racemic forms, like the diastereomers, can be separated in a known manner to give the stereoisomerically uniform constituents (cf. E. L. Eliel, Stereo-chemistry of Carbon Compounds, McGraw Hill, 1962). What follows are examples of isomeric forms of the cycloalkano[b]dihydroindole- and -indolesulphonamides:

a) Cycloalkano[b]indole-sulphonamides

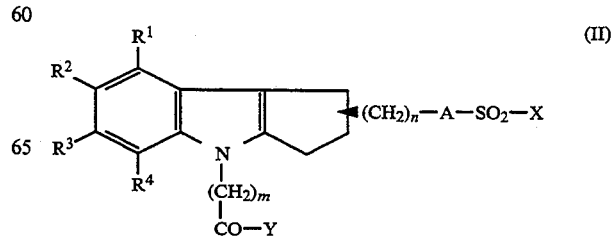

-continued

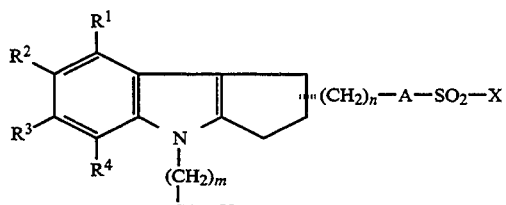
(III)

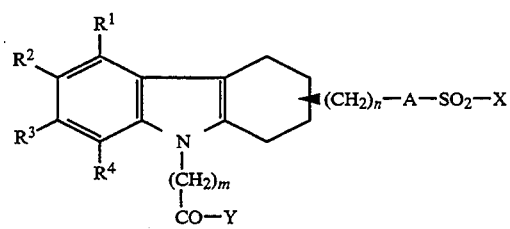
(IV)

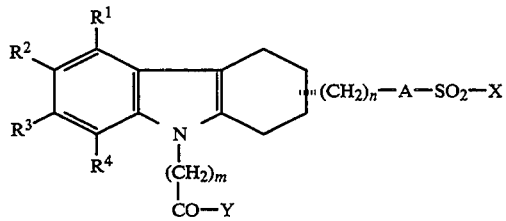
(V)

b) Cycloalkano[b]dihydroindolesulphonamides

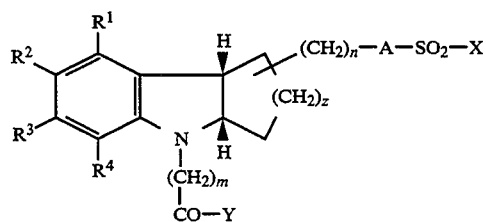
(VI)

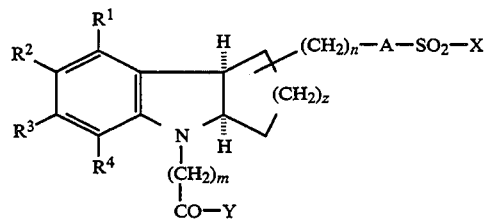
(VII)

where $R^1$, $R^2$, $R^3$, $R^4$, A, X, Y, m, n and z have the above-mentioned meanings.

The substituted cycloalkano[b]dihydroindole- and -indole-sulphonamides according to the invention can also be in the form of their salts. Salts which may be mentioned in general in this connection are salts with organic or inorganic bases.

Physiologically tolerable salts are preferred within the scope of the present invention. Physiologically tolerable salts of the substituted cycloalkano[b]-dihydroindole- and -indole-sulphonamides can be metal salts or ammonium salts of the substances according to the invention which have a free carboxyl group. Examples of particularly preferred salts are sodium, potassium, magnesium or calcium salts and ammonium salts which are derived from ammonia or organic amines, such as, for example, ethylamine, di- or triethylamine, di- or tri-ethanolamine, dicyclohexylamine, dimethylaminoethanol, arginine, lysine or ethylenediamine.

Surprisingly, the substances according to the invention are active as inhibitors of thrombocyte aggregation, furthermore cause inhibition of thromboxane synthase on isolated platelets, and can be used for therapeutic treatments of humans and animals.

Preferred compounds of the general formula (I) are those in which $R^1$, $R^2$, $R^3$ and $R^4$ are identical or different and
represent hydrogen, fluorine, chlorine, bromine, iodine, nitro, cyano, trifluoromethyl, carboxyl, hydroxyl or trifluoromethoxy, or represent a group of the formula $-S(O)_w R^5$ where
$R^5$—represents straight-chain or branched alkyl having up to 6 carbon atoms, or represents phenyl which, in turn, can be substituted by fluorine, chlorine, bromine, nitro, cyano or trifluoromethyl, w—represents a number 0, 1 or 2, represent straight-chain or branched alkoxy or alkoxycarbonyl, each of which has up to 8 carbon atoms, or represent a group of the formula $-NR^6R^7$ where
$R^6$ and $R^7$ are identical or different and denote hydrogen, straight-chain or branched alkyl having up to 6 carbon atoms or phenyl or represent cyclopropyl, cyclopentyl, cyclohexyl or phenyl, or represent straight-chain or branched alkyl or alkenyl, each of which has up to 8 carbon atoms, and each of which is optionally substituted by fluorine, chlorine, bromine, hydroxyl, carboxyl, cyano, phenyl, straight-chain or branched alkyl, alkoxy or alkoxycarbonyl, each of which has up to 6 carbon atoms, or by a group of the formula $-S(O)_w R^5$ or $-NR^6R^7$ where
w, $R^5$, R6 and $R^7$ have the abovementioned meanings, X—represents phenyl which can optionally be up to tetrasubstituted by identical or different substituents from the series comprising nitro, hydroxyl, fluorine, chlorine, bromine, iodine, cyano, trifluoromethyl, trifluoromethoxy, hydroxyl, carboxyl, phenyl, phenoxy, straight-chain or branched alkoxy or alkoxycarbonyl, each of which has up to 6 carbon atoms, or by straight-chain or branched alkyl having up to 6 carbon atoms, or represents straight-chain or branched alkyl having up to 6 carbon atoms or trifluoromethyl, m—represents the number 1, 2, 3 or 4, n—represents the number 0 or 1, z—represents the number 1, 2 or 3, A—represents a direct bond or the —NH group, and Y—represents hydroxyl, alkoxy having up to 6 carbon atoms, phenoxy or the group $-NR^6R^7$, where $R^6$ and $R^7$ have the abovementioned meanings, or represents a group of the formula $-NHSO_2-R^5$ where $R^5$—has the abovementioned meaning, with the proviso that, in all cases, two of the substituents $R^1-R^4$ are other than hydrogen in the event that m denotes the number 2 and Y represents the hydroxyl group, if appropriate in an isomeric form, and salts of these compounds.

Particularly preferred compounds of the general formula (I) are those in which $R^1$, $R^2$, $R^3$ and $R^4$ are identical or different and represent hydrogen, fluorine or chlorine, represent a group of the formula —S(O)$_w$—R$^5$ where
- R$^5$—represents straight-chain or branched alkyl having up to 4 carbon atoms, or represents phenyl which, in turn, can be substituted by fluorine, chlorine or bromine and
- w—denotes the number 2, represent straight-chain or branched alkoxy or alkoxycarbonyl, each of which has up to 4 carbon atoms, represent the group of the formula —NR$^6$R$^7$ where
- R$^6$ and R$^7$ are identical or different and
  - denote hydrogen, straight-chain or branched alkyl having up to 4 carbon atoms or phenyl, or
- represent straight-chain or branched alkyl having up to 6 carbon atoms which is optionally substituted by fluorine, chlorine, bromine, hydroxyl, cyano or phenyl, X—represents phenyl which is optionally up to trisubstituted by identical or different substituents from the series comprising fluorine, chlorine, bromine, cyano, trifluoromethyl, trifluoromethoxy or by straight-chain or branched alkyl, alkoxy and alkoxycarbonyl, each of which has up to 4 carbon atoms, m—represents the number 1, 2, 3 or 4, n—represents the number 0 or 1, z—represents the number 1 or 2, A—represents the —NH group, and Y—represents hydroxyl, alkoxy having up to 4 carbon atoms, phenoxy or the group of the formula —NR$^6$R$^7$ where
- R$^6$ and R$^7$ have the abovementioned meanings, or represents a group of the formula —NHSO$_2$—R$^5$ where
- R$^5$ has the abovementioned meaning, with the proviso that, in all cases, two of the substituents R$^1$—R$^4$ are other than hydrogen in the event that m denotes the number 2 and Y represents the hydroxyl group, if appropriate in an isomeric form, and salts of these compounds.

The compounds of the general formula (I) can be prepared

[A] by reacting compounds of the general formula (VIII)

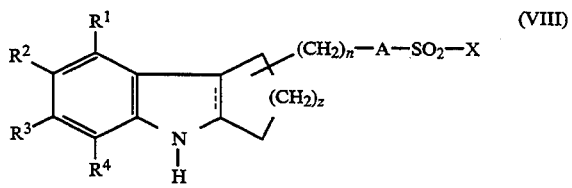

in which
R$^1$, R$^2$, R$^3$, R$^4$, n, z, A and X have the abovementioned meanings, in the event that m represents the number 2, by initially reacting acrylonitrile in inert solvents, if appropriate in the presence of a base, to give the corresponding cyanoethyl compounds and then hydrolyzing these compounds to give the corresponding acids (Y=OH), or

[B] by reacting compounds of the general formula (IX)

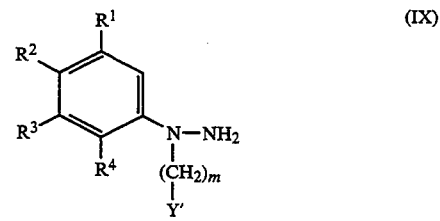

in which
R$^1$, R$^2$, R$^3$, R$^4$ and m have the abovementioned meanings and
Y'—represents (C$_1$—C$_4$)-alkoxycarbonyl or cyano, with cycloalkanonesulphonamides of the general formula (X)

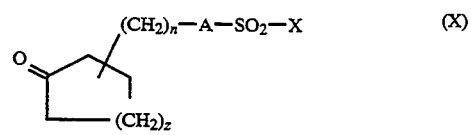

in which z, n, A and X have the abovementioned meanings, in inert solvents, if appropriate in the presence of a catalyst, and furthermore, in the case of the acids (Y=OH), hydrolyzing the esters by a conventional method, in the case of variation of the esters (Y=alkoxy, C$_1$-C$_8$-phenoxy), reacting the acids with the corresponding alcohols in the presence of a catalyst by a customary method, if appropriate in inert solvents, in the case of the amides and sulphonamides (Y=—NR$^6$R$^7$, —NHSO$_2$—R$^5$), reacting either the esters directly, or the acids thereof by conventional activation, with the amines or sulphonamides of the general formulae (XIa) and (XIb)

HNR$^6$R$^7$  (XIa)

NH$_2$—SO$_2$—R$^5$  (XIb)

in which
R$^5$, R$^6$ and R$^7$ have the abovementioned meanings, if appropriate in the presence of a catalyst, in the case of the cycloalkano[b]dihydroindolesulphonamides, reducing the cycloalkano[b]indolesulphonamides in the presence of a reducing agent in inert solvents, separating the isomers, if appropriate, and in the case of salt formation, reacting the product with a suitable base.

The process according to the invention can be illustrated for example by the following equation:
[A]

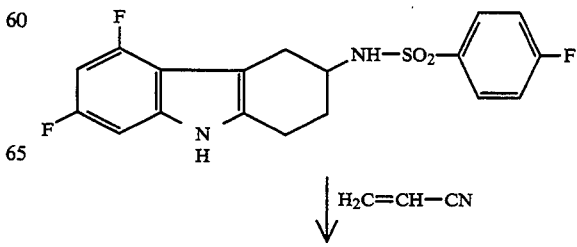

-continued

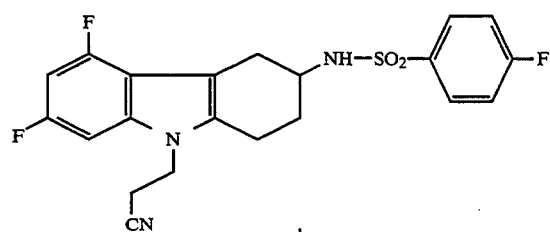

| Hydrolysis ↓

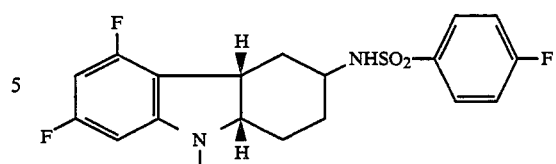

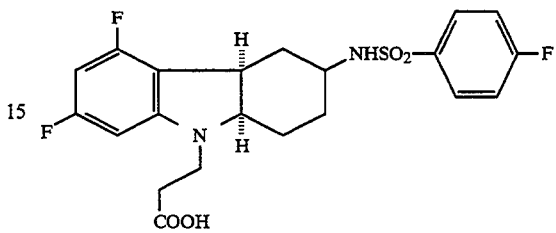

[B]

Reduction ↓

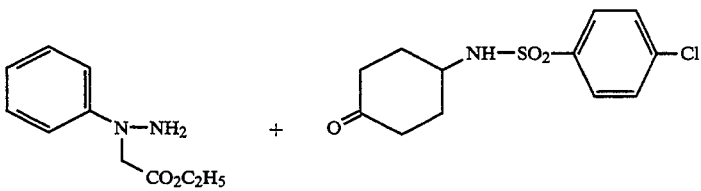

↓

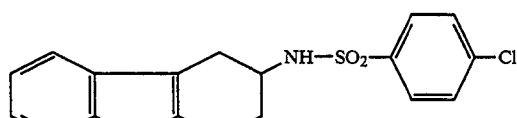

+NH₃ ↙    ↘ 1) NaOH  2) HCl

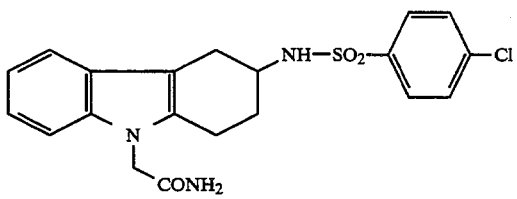

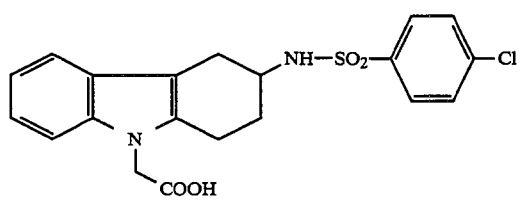

Solvents which can be used for processes [A] and [B] according to the invention are water and organic solvents which do not undergo changes under the reaction conditions. These preferably include chlorinated hydrocarbons, such as, for example, chloroform or methylene chloride, alcohols, such as methanol, ethanol, propanol or isopropanol, ethers, such as diethyl ether, tetrahydrofuran, dioxane, glycol monomethyl ether or glycol dimethyl ether, hydrocarbons, such as benzene, toluene, xylene, cyclohexane, hexane or mineral oil fractions, dimethylsulphoxide, dimethylformamide, hexamethylphosphoric triamide, ethyl acetate, acetonitrile or pyridine. It is also possible to use mixtures of the solvents mentioned.

Bases which can be used for processes [A] and [B] according to the invention are customary basic compounds. These preferably include alkali metal hydroxides and alkaline earth metal hydroxides, such as lithium hydroxide, sodium hydroxide, potassium hydroxide or barium hydroxide, alkali metal hydrides, such as sodium hydride, alkali metal carbonates or alkaline earth metal carbonates, such as sodium carbonate or potassium carbonate, or alkali metal alkoxides, such as, for example, sodium methoxide, sodium ethoxide, potassium methoxide, potassium ethoxide or potassium tert. -butoxide, or amides, such as sodium amide or lithium diisopropylamide, or organic amines or ammonium salts, such as benzyltrimethylammonium hydroxide, tetrabutylammonium hydroxide, pyridine, triethylamine or N-methylpiperidine.

Processes [A] and [B] according to the invention are generally carried out in a temperature range of 0° C. to 150° C., preferably of 0° C. to 100° C.

Processes [A] and [B] are generally carried out under atmospheric pressure. However, it is also possible to carry out the processes in a vacuum or under super-atmospheric pressure (for example from 0.5 to 5 bar).

The esters are hydrolyzed by a customary method, by treating the esters in inert solvents with customary bases, it being possible to convert the initially resulting salts into the free carboxylic acids by treating them with acid.

Bases which are suitable for the hydrolysis are the customary inorganic bases. These preferably include alkali metal hydroxides or alkaline earth metal hydroxides, such as, for example, sodium hydroxide, potassium hydroxide or barium hydroxide, or alkali metal carbonates, such as sodium carbonate or potassium carbonate.

Solvents which are suitable for the hydrolysis are water or the organic solvents which are customary for hydrolysis. These preferably include alcohols, such as methanol, ethanol, propanol, isopropanol or butanol, or ethers, such as tetrahydrofuran or dioxane, or dimethylformamide or dimethyl sulphoxide. Solvents which are particularly preferably used are alcohols, such as methanol, ethanol, propanol or isopropanol. It is also possible to employ mixtures of the solvents mentioned.

The hydrolysis is generally carried out within a temperature range of 0° C. to +140° C., preferably of +20° C. to +100° C.

The hydrolysis is generally carried out under atmospheric pressure. However, it is also possible to carry out the hydrolysis in a vacuum or under super-atmospheric pressure (for example from 0.5 to 5 bar).

When carrying out the hydrolysis, the base is generally employed in an amount of 1 to 5 moles, preferably of 1 to 2 moles, based on 1 mole of the ester. It is particularly preferred to use molar amounts of the reactants.

When the reaction is carried out, the first step gives the salt of the compounds according to the invention as intermediates which can be isolated. The acids according to the invention are obtained by treating the salts with customary inorganic acids. These preferably include mineral acids, such as, for example, hydrochloric acid, hydrobromic acid, sulphuric acid or phosphoric acid. In connection with the preparation of the carboxylic acids, it has proven advantageous to acidify the basic reaction mixture of the hydrolysis reaction in a second step without the salts being isolated. The acids can then be isolated in a customary manner.

The acids are esterified by a customary method, by reacting the acids with the appropriate alcohols in the presence of a catalyst and, if appropriate, in one of the abovementioned solvents. It is preferred to employ this alcohol also as the solvent.

Catalysts which can be employed are inorganic acids, such as, for example, sulphuric acid or inorganic acid chlorides, such as, for example, thionyl chloride.

In general, 0.01 to 1, preferably 0.05 to 0.5, mole of catalyst are employed per mole of reactant.

The amidation is carried out in one of the above-mentioned solvents, preferably in alcohols, such as ethanol or methanol, within a temperature range of 0° C. to +50° C., preferably of +10° to +30° C., and under atmospheric pressure.

If appropriate, both the esterification and the amidation ($Y=NR^6R^7$, $—NHSO_2R^5$) can proceed via the activated step of the acid halides (I, Y=halogen), which can be prepared from the corresponding acid by reaction with thionyl chloride, phosphorus trichloride, phosphorus pentachloride, phosphorus tribromide or oxalyl chloride.

The amidation with the sulphonamides of the general formula (XIb) can also proceed via the step of the acids (R, Y=OH) in the presence of condensation agents, such as, for example, N, N′-dicyclohexylcarbodiimide, or by activation, for example, by reaction to form the corresponding imidazolides, according to customary methods.

Some of the compounds of the general formula (VIII) are new. They can be prepared by reacting phenylhydrazines of the general formula (XII)

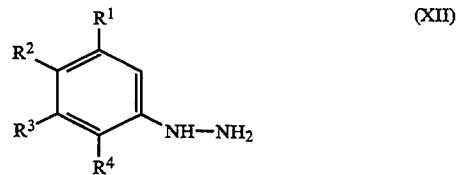

(XII)

in which $R^1 R^2$, $R^3$ and $R^4$ have the abovementioned meanings, with cycloalkanonesulphonamides of the general formula (X)

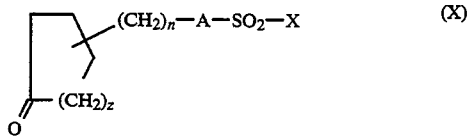

(X)

in which

A, X, n and z have the abovementioned meanings, in the presence of the abovementioned inert solvents and if appropriate in the presence of a catalyst.

The reaction with phenylhydrazines of the formula (XII) proceeds under the reaction conditions described in the case of process (B).

Examples of hydrazines which are employed in the process according to the invention are: phenylhydrazine, 4-methoxyphenylhydrazine, 4-chlorophenylhydrazine, 4-fluorophenylhydrazine, 4-methylphenylhydrazine, 2,4-difluorophenylhydrazine, 3,5-difluorophenylhydrazine, 3-fluorophenylhydrazine and 2-fluorophenylhydrazine.

Some of the phenylhydrazines of the general formula (XII) are known or can be prepared by a customary method [cf. Houben-Weyl, "Methoden der organischen Chemie [Methods in Organic Chemistry]", X/2, page 1, 123, 693].

The cycloalkanonesulphonamides of the general formula (X) and their preparation are known [cf. DOS (German Published Specification) 3,631,824].

The pure enantiomeric compounds of the general formula (I) according to the invention can be obtained by customary methods, e.g. analogously to the process described in DOS (German Published Specification) 3,631,824.

The compounds of the general formula (IX) are known per se or can be prepared by a customary method [cf. DOS (German Published Specification) 2,312,256].

The amines of the general formula (XIa) are known [cf. Houben-Weyl, "Methoden der organischen Chemie [Methods in Organic Chemistry]", Volumes XI/1 and XI/2].

The sulphonamides of the general formula (XIb) are likewise known [cf. Beilstein, 11, 26].

The substituted cycloalkano[b]indole- and -dihydroindlesulphonamides or their salts can be employed as active compounds in medicaments. The active compounds are active as inhibitors of thrombocyte aggregation and as thromboxane $A_2$-antagonists, and they cause inhibition of thromboxane synthase on isolated platelets. They can preferably be employed in the treatment of thromboses, thromboembolisms and ischaemias, and in the prophylaxis of myocardial infarct as antiasthmatics and antiallergics.

To determine the action as an inhibitor of thrombocyte aggregation, blood was used from healthy subjects of both sexes. 9 parts of blood were treated with one part of 3.8% strength aqueous sodium citrate solution as an anticoagulant. From this blood, platelet-rich citrated plasma (PRP)[1] is obtained (Jürgens/Beller, Klinische Methoden der Blutgerinnungsanalyse [Clinical Methods in Blood Coagulation Analysis]; Thieme Verlag, Stuttgart, 1959).

For these assays, 0.8 ml of(PRP)[1] and 0.1 ml of the active compound solution were preincubated at 37° C. in a water bath. The thrombocyte aggregation was then determined in an aggregometer at 37° C. (Therapeutische Berichte 47, 80–86, 1975) by means of turbidometry (Born, G. V. R., J. Physiol. (London), 162, 67, 1962). For this purpose, the preincubated sample was treated with 0.1 ml of collagen, an agent which triggers aggregations. The(PRP)[1] sample underwent changes in optical density, which was recorded during a period of 6 minutes, and the response was determined after 6 minutes. From this, the inhibition compared with the control is calculated as a percentage. The limiting concentration given is the range of the minimum effective concentration.

The limiting concentrations are between 0.01 and 10 mg/l.

| Example No. | EC in mg/l |
| --- | --- |
| 4 | 0.01–0.03 |
| 8 | 0.3–1.0 |
| 15 | 0.01–0.03 |

Measurement of thromboxane synthase on washed human thrombocytes

1. Preparation of thrombocyte suspensions

Blood from healthy donors is taken up in EDTA (1% strength in 0.9% NaCl, 9+1), and the mixture is centrifuged for 20 minutes at 1,000 rpm (150 g). The platelet-rich plasma (PRP)[2] is pipetted off, and 10 ml batches are centrifuged for 20 minutes at 2,500 rpm. The platelet-rich plasma[2] is decanted off.

The remaining platelets are suspended in 5 ml of resuspension buffer (0.15M TRIS/0.9% of NaCl/77 mmol EDTA, 8:91:1; pH 7.4 set using 1N HCl), the suspension is centrifuged for 20 minutes at 2,500 rpm and suspended in 1 ml of resuspension buffer. A thrombocyte titer of $3 \times 10^5/\mu l$ is established.

2. Measurement of thromboxane synthase 1 ml of the platelet suspension and 0.01 ml of the test preparation in a 10% strength DMSO solution are incubated for 2 minutes at 37° C. To this is added 0.1 ml of $^3$H-arachidonic acid Amersham Buchler GmbH and Co. KG ($6.6 \times 10^{-5}$ mol/l) of a specific activity of 140 MBq/mmol, and incubation is continued at 37° C. for 10 minutes. After the reaction, the mixture is acidified using about 0.02 ml of 0.5N citric acid and immediately extracted 3 times using 1 ml of ethyl acetate each time. The supernants are collected in 10 ml glass tubes, and the ethyl acetate is removed by blowing in $N_2$ at 25° C. The residue is taken up in 50 $\mu l$ of MeOH/CHCl$_3$ (1:1) and the fluid is applied to TLC glass plates (Silica gel 60 F254 20×20 cm, by Merck).

The separation is performed in a mobile phase mixture CHCl$_3$/MeOH/glacial acetic acid/H$_2$O (80:8:1:0.8). The radioactive distribution is recorded in a TLC scanner Ramona-Ls, made by Raytest, and evaluated quantitatively using an integration programme.

The concentration of test substances which lead to a 50% inhibition of thromboxane formation, compared with the control, is determined.

Inhibition of thromboxane synthesis on washed platelets from human blood.

| Example No. | IC$_{50}$ mol/l |
| --- | --- |
| 4 | $1-3 \times 10^{-6}$ |

The novel active compounds can be converted in a manner known per se into the customary formulations, such as tablets, capsules, coated tablets, pills, granules, aerosols, syrups, emulsions, suspensions and solutions, with inert non-toxic, pharmaceutically acceptable excipients or solvents being used. In this connection, the therapeutically active compound should be present in each case in a concentration of about 0.5 to 90% by weight, preferably of 5 to 70% by weight, based on the preparation, which is sufficient to achieve the stated dosage range.

For example, the formulations are prepared by extending the active compounds with solvents and/or excipients, if appropriate with the use of emulsifiers and/or dispersants, it being possible, for example when water is used as the diluent, to use organic solvents as auxiliary solvents, if necessary.

Examples of auxiliaries which may be mentioned are: water, non-toxic organic solvents, such as paraffins (for example mineral oil fractions), vegetable oils (for example groundnut/sesame seed oil), alcohols (for example ethyl alcohol, glycerol), glycols (for example propylene glycol, propylethylene glycol), solid excipients, such as, for example, ground natural rocks (for example kaolins, clays, talc, chalk), ground synthetic rocks (for example highly-disperse silica, silicates), sugars (for example sucrose, lactose and fructose), emulsifiers (for example polyoxyethylene fatty acid esters, polyoxyethylene fatty alcohol ethers, alkylsulphonates and arylsulphonates), dispersants (for example lignin, sulphite wet liquors, methylcellulose, starch and polyvinylpyrrolidone) and lubricants (for example magnesium stearate, talc, stearic acid and sodium laurylsulphate).

The application can be carried out in a customary manner, preferably orally or parenterally, in particular perlingually or intravenously. In the case of oral application, tablets can, of course, also contain additives, such as sodium citrate, calcium carbonate and dicalcium phosphate together with various adjuvants, such as starch, preferably potato starch, gelatin, etc., besides the excipients mentioned. Lubricants, such as magnesium stearate, sodium laurylsulphate and talc can furthermore be used for tablet-making. In the case of aqueous suspensions and/or elixirs which are intended for oral administration, it is possible to add various flavor improvers or colorants to the active substances, in addition to the abovementioned auxiliaries.

In the case of parenteral administration, active compound solutions can be employed using suitable liquid excipients.

In general, it has proven advantageous to administer amounts of about 0.001 to 1 mg/kg, preferably about 0.01 to 0.5 mg/kg, of body weight to achieve effective results on intravenous administration. In the case of oral administration, the dosage is generally about 0.01 to 20 mg/kg, preferably 0.1 to 10 mg/kg, of body weight.

However, occasionally it can be advantageous to deviate from the figures mentioned, and to do so as a function of the body weight or the type of administration route, of the individual behavior towards the medicament, the nature of its formulation and the point in time, or interval, at which the medicament is administered. For instance, it may suffice in some cases to make do with less than the previously mentioned minimum amount, while in other cases the upper limit specified must be exceeded. In the case where relatively large amounts are administered, it may be advisable to divide the latter into several individual doses taken over one day.

Starting compounds

EXAMPLE I 3,5-Difluorophenylhydrazine

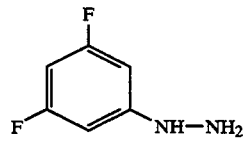

30.50 g (2.363 mmol) of 3,5-difluoroaniline are suspended in 128 ml (700 mmol) of 20% strength HCl, and the suspension is stirred with 16.46 g (236.3 mmol) of sodium nitrite in 95 ml of water at temperatures of below 5° C. The mixture is then stirred for 30 minutes at 0° C. so that the solid dissolves almost completely. The cold solution is added in portions to 769 g (2.95 mol) of a 40% strength sodium bisulphite solution with cooling, the mixture being maintained at a pH of 6.5 with 2N sodium hydroxide solution. The mixture is now refluxed for 4 hours, the pH of 6.5 being checked every 30 minutes and, if appropriate, readjusted. After cooling, the mixture is rendered alkaline using 1N sodium hydroxide solution and extracted 5 times using 400 ml of $CH_2Cl_2$ each time, the extract is dried using $Na_2SO_4$ and the solvent is evaporated off, and the residue is stirred with petroleum ether and dried in a high vacuum.

Yield: 17.34 g (120.3 mmol; 51% of theory) M.p.: 93°–95° C. $R_f = 0.9$ (ethyl acetate)

EXAMPLE II 3-(4-Chlorophenylsulphonamido)-5,7-difluoro-1,2,3,4-tetrahydrocarbazole

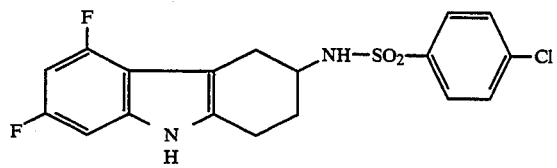

14.0 g (97 mmol) of the compound of Example I and 27.95 g (97 mmol) of 4-chloro-N-(4-oxo-cyclohexyl)-benzenesulphonamide are refluxed for 5 hours in 190 ml of ethanol and 36 ml of concentrated sulphuric acid, then the mixture is cooled and diluted with 300 ml of water. The mixture is extracted 4 times using 250 ml of ethyl acetate each time, and the organic phase is dried using sodium sulphate, filtered with suction over kieselguhr and evaporated. The residue is stirred with methylene chloride and dried in a high vacuum.

Yield: 37.6 g (95 mmol; 98% of theory) M.p.: 171°–174° C.

EXAMPLE III 3-(4-Chlorophenylsulphonamido)-9-(2-cyanoethyl)-5,7-difluoro-1,2,3,4-tetrahydrocarbazole

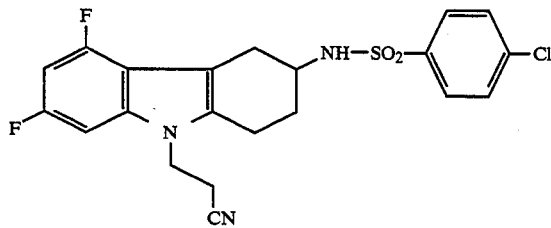

5.95 g (15.0 mmol) of the compound from Example II are dissolved under argon in 30 ml of dimethylformamid, analytical grade, and 495 mg (16.5 mmol) of 80% sodium hydride in paraffin oil are added at room temperature with stirring. When the evolution of hydrogen has ceased, 1.75 g. (33.0 mmol) of acrylonitrile are added and the mixture is stirred for 30 minutes. If the starting material has not disappeared completely (TLC check/toluene: ethyl acetate=4:1), another 0.23 g (4.3 mmol) of acrylonitrile are added and the mixture is again stirred for 30 minutes. 50 ml of ethyl acetate are added, and the mixture is shaken 3 times using 50 ml of 1N sulphuric acid each time, and the organic phase is dried using sodium sulphate and evaporated. The residue is chromatographed on Silica gel 60 (Merck/particle size 40–63 μm/eluent first toluene, then increasing proportions of ethyl acetate, ending with pure ethyl acetate).

Yield: 4.50 g (10.0 mmol; 67% of theory) M.p.: 114°–117° C. R_f=0.24 (toluene/ethyl acetate=4:1)

Preparation Example (Formula I)

EXAMPLE 1

3-(4-Chlorophenylsulphonamido)-9-(2-carboxyethyl)-5,7-difluoro-1,2,3,4-tetrahydrocarbazole

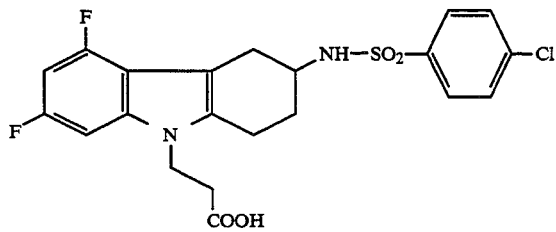

3.05 g (6.8 mmol) of the compound from Example III are dissolved in 20 ml of ethanol, 100 ml of 10% strength sodium hydroxide solution are added, and the mixture is then stirred under reflux for 16 hours. The cooled batch is extracted by shaking twice using 50 ml of methylene chloride each time, and a pH of 1 is established at 0° C., using 6N hydrochloric acid. The precipitate which has separated out is filtered off with suction, washed with water to neutrality, dried in a high vacuum over phosphorus pentoxide and sodium hydroxide, and weighed.

Yield: 2.73 g (5.8 mmol; 86% of theory) M.p.: 134° C.

The compounds listed in Table 1 can be prepared analogously, using the procedure for Example 1:

TABLE 1

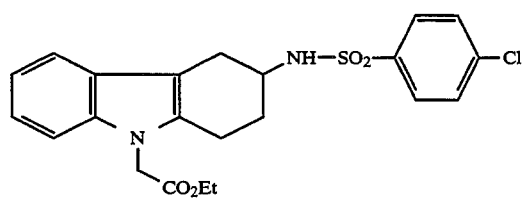

| Example No. | $R^1$ | $R^2$ | $R^3$ | $R^4$ | X  | $R_f$ value* |
|-------------|-------|-------|-------|-------|----|--------------|
| 2           | F     | H     | F     | H     | F  | 0.33         |
| 3           | H     | F     | H     | F     | F  | 0.39         |
| 4           | H     | F     | H     | F     | Cl | 0.31         |

*Mobile phase: dichloromethane/methanol = 10:1

EXAMPLE 5

3-(4-Chlorophenylsulphonamido)-9-(2-ethoxycarbonylmethyl)-1,2,3,4-tetrahydrocarbazole

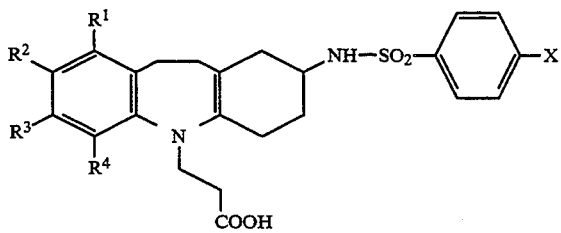

6.2 g (21.5 mmol) of 4-chloro-N-(4-oxo-cyclohexyl)-benzenesulphonamide and 4.2 g (21.5 mmol) of (1-phenylhydrazine) acetic acid ethyl ester are refluxed for 6 hours in 30 ml of ethanol and 5 ml of concentrated sulphuric acid. After the mixture has cooled, 70 ml of water are added and the mixture is extracted 5 times using 40 ml of ethyl acetate each time. The organic phase is dried using sodium sulphate and evaporated. The crude product is purified by chromatography on Silica gel 60 (Merck/particle size 63–200 μm), using methylene chloride as the mobile phase.

Yield: 5.1 g (11.4 mmol; 53% of theory) M.p.: 64°–66° C. R_f=0.45 (dichloromethane)

EXAMPLE 6

3-(4-Chlorophenylsulphonamido)-9-(2-carboxymethyl)-1,2,3,4-tetrahydrocarbazole

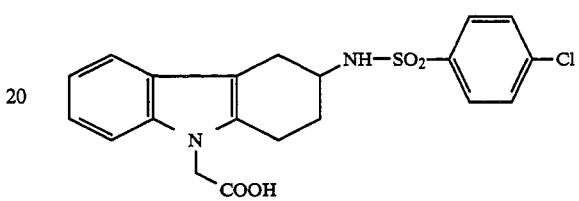

3.5 g (7.8 mmol) of the compound from Example 5 are dissolved in 30 ml of ethanol, 16 ml of 1N sodium hydroxide solution are added, and the mixture is stirred at room temperature for 2 hours. The solvent is evaporated off, the residue is taken up in 50 ml of water, and the mixture is extracted twice using 20 ml of methylene chloride each time. After the mixture has been acidified using 2N sulphuric acid (pH=1), it is extracted 3 times using 30 ml of ethyl acetate each time, the combined organic phases are dried using sodium sulphate, and the solvent mixture is evaporated off. The resulting foam, which solidifies in a high vacuum, is soluble in ether, from which it reprecipitates on scratching.

Yield: 2.32 g (5.5 mmol/71% of theory) Melting point: 172°–174° C.

EXAMPLE 7

3-(4-Chlorophenylsulphonamido)-6-fluoro-9-(2-methoxycarbonylethyl)-1,2,3,4-tetrahydrocarbazole

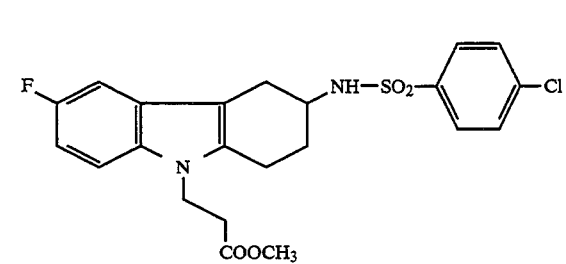

2.5 g (5.55 mmol) of 3-(4-chlorophenylsulphonamido)-6-fluoro-9-(2-carboxyethyl)-1,2,3,4-tetrahydrocarbazole are treated with 50 ml of absolute methanol and 1 ml of concentrated sulphuric acid. The mixture is stirred at reflux temperature for 2 hours and concentrated on a rotary evaporator. The crystalline residue obtained on evaporation is stirred with ether, the solids are filtered off with suction and then recrystallized from methanol. This gives 2.0 g of colorless crystals (77.5% of theory).

Melting point: 143° C. Thin-layer chromatography in the mobile phase system toluene/ethanol=6:1 R_f=0.23

The examples listed in Table 2 were prepared analogously to Example 7:

TABLE 2

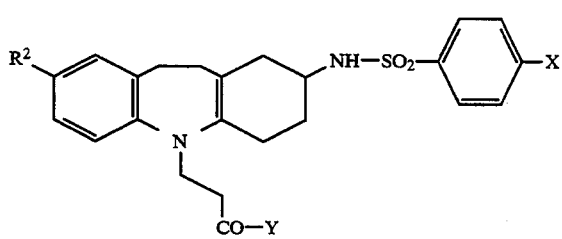

| Example No. | R² | Y | X | Melting point/ R_f value* |
|---|---|---|---|---|
| 8 | F | —OC₂H₅ | Cl | 122° C.ᵃ⁾ |
| 9 | F | —O—CH(CH₃)₂ | Cl | 152° C.ᵇ⁾ |
| 10 | H | —OC₃H₇-i | F | 0.54ᵃ⁾ |
| 11 | H | —OC₂H₅ | F | 0.52ᵃ⁾ |
| 12 | H | —OCH₃ | F | 0.52ᵃ⁾ |

R_f values*
Mobile phase systems:
ᵃ⁾toluene/ethanol (6:1)
ᵇ⁾toluene/ethanol (10:1)

Merck TLC aluminum roll, Silica gel 60, code No. 5562

EXAMPLE 13

3-(4-Fluorophenylsulphonamido)-9-(2-carbamoylethyl)-1,2,3,4-tetrahydrocarbazole

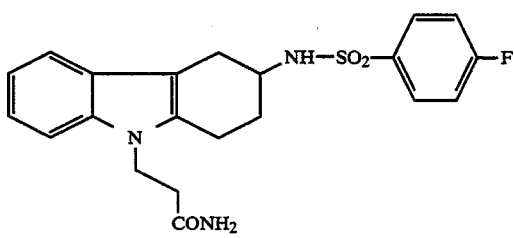

1 g (2.18 mmol) of the compound from Example 11 is treated with 20 ml of a 6N ammonia solution in methanol, and the mixture is allowed to stand for 3 days at room temperature. It is then concentrated, and the residue is purified by flash chromatography in the mobile phase system toluene/ethyl acetate (3:1, 1:1) and then in the mobile phase system toluene/ethanol (10:1, 5:1) using a column packed with 40 g of Silica gel 60. The fractions are concentrated, and a colorless foam is obtained.

Yield: 0.52 g (55.9% of theory) R_f value=0.26 (toluene/ethanol 6:1, Merck TLC aluminum roll, Silica gel 60 code No. 5562).

The compounds listed in Table 3 were prepared from the corresponding esters in analogy with the procedure of Example 13:

TABLE 3

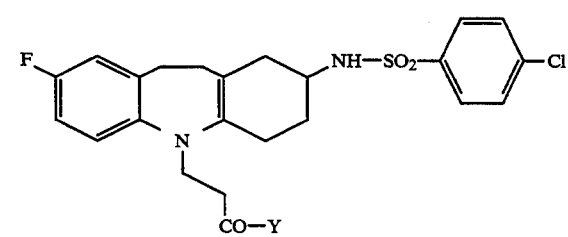

TABLE 3-continued

| Example No. | Y | Melting point (°C.) |
|---|---|---|
| 14 | —N(CH₃)₂ | 224 |
| 15 | —NH₂ | 214 |

EXAMPLE 16

3-(R)-(4-Fluorophenylsulphonamido)-9-[2-(N-phenylsulphonecarbamoyl)-ethyl]-1,2,3,4-tetrahydrocarbazole

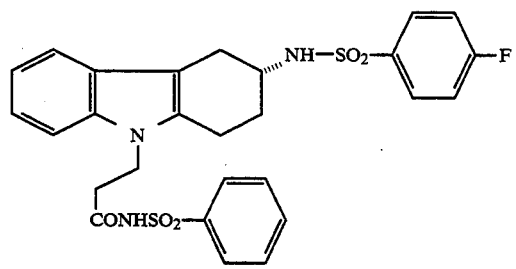

4.16 g (10.0 mmol) of (R)-3-(4-fluorophenylsulphonamido)-9-(2-carboxyethyl)-1,2,3,4-tetrahydrocarbazole are dissolved in 70 ml of methylene chloride, analytical grade, and the solution is treated with 1.58 g (10 mmol) of benzene sulphonamide. 2 ml of dimethylformamide together with 2.3 g (12.0 mmol) of N-(3-dimethylaminopropyl)-N'-ethylcarbodiimide hydrochloride in 25 ml of methylene chloride and 1.7 ml (12 mmol) of triethylamine are then added to dissolve, and the mixture is stirred for 24 hours at room temperature. The reaction mixture is washed twice using 40 ml of 2N sulphuric acid each time, once using 50 ml of saturated sodium bicarbonate solution and once using saturated sodium chloride solution, dried over sodium sulphate, concentrated and freed from residual solvent in a high vacuum. Column chromatography (Merck Silica gel, 40–60 μm/methylene chloride: methanol=15:1) gives 2.56 g (4.6 mmol) of product. R_f=0.62 (methylene chloride/methanol=10:1)

The examples listed in Table 4 are prepared analogously to the procedure of Example 16:

TABLE 4

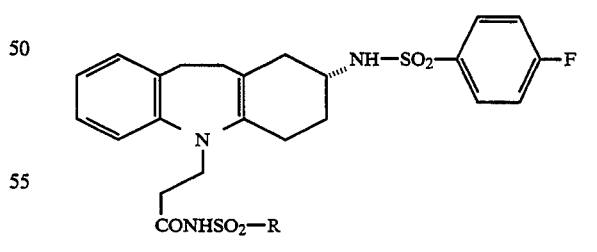

| Example No. | R | R_f | Mobile phase |
|---|---|---|---|
| 17 | —CH₃ | 0.45 | Toluene/acetone 4:1 |
| 18 | ⌬—Cl | 0.29 | Toluene/acetone 3:1 |

The examples listed in Table 5 are prepared analogously to the procedure of Example 6.

TABLE 5

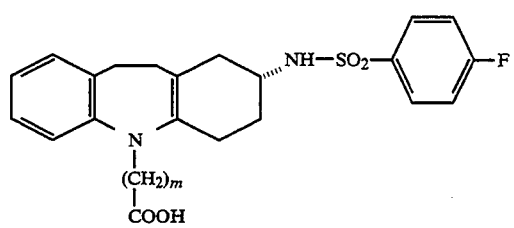

| Example No. | m | $R_f$ | Mobile phase |
|---|---|---|---|
| 19 | 3 | 0,49 | Dichlormethane/methanol 10:1 |
| 20 | 4 | 0,66 | Ethylacetate |

It will be appreciated that the instant specification is set forth by way of illustration and not limitation, and that various modifications and changes may be made without departing from the spirit and scope of the present invention.

What is claimed is:

1. A substituted cycloalkano[b]dihydroindole- or indole-sulphonamide of the formula

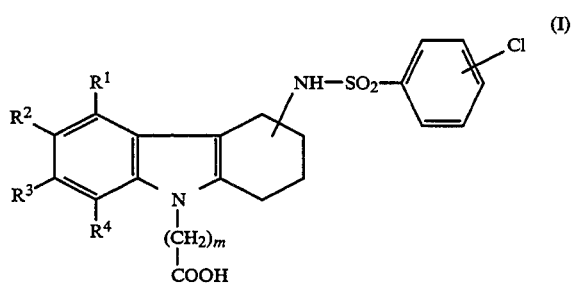

(I)

in which $R^1$, $R^2$, $R^3$, $R^4$ as identical or different and represent hydrogen or fluorine provided that at least two of these substituents are fluorine, and m represents 1, 2, 3 or 4 or salt thereof.

2. A compound according to claim 1, wherein such compound is 3-(4-chlorophenylsulphonamido)-9-(2-carboxyethyl)-5,7-difluoro-1,2,3,4-tetrahydrocarbazole of the formula

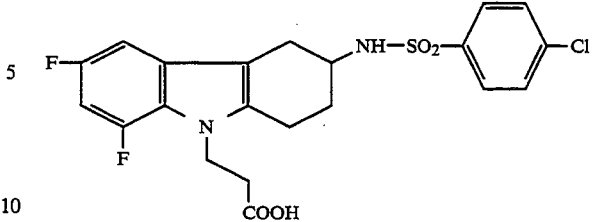

or a salt thereof.

3. A compound according to claim 1, wherein such compound is 3-(4-chlorophenylsulphonamido)-9-(2-carboxyethyl)-6,8-difluoro-1,2,3,4-tetrahydrocarbazole of the formula

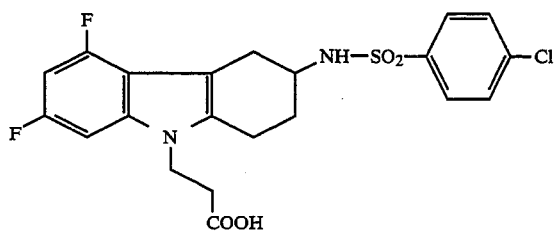

or a salt thereof.

4. A composition for the treatment of thromboses, thromboembolisms, ischaemias, asthma and allergies, and for the prophylaxis of myocardia infarct comprising an amount effective therefor of a compound or salt thereof according to claim 1 and a pharmacologically acceptable diluent.

5. The method of treating thromboses, thromboembolisms, ischaemias, asthma and allergies, and for the prophylaxis of myocardial infarct in a patient in need thereof which comprises administering to such patient an amount effective therefor of a compound or salt thereof according to claim 1.

6. The method according to claim 3, wherein such compound is 3-(4-chlorophenylsulphonamido)-9-(2-carboxyethyl)-5,7-difluoro-1,2,3,4-tetrahydrocarbazole, or 3-(4-chlorophenylsulphonamido)-9-(2-carboxyethyl)-6,8-difluoro-1,2,3,4-tetrahydrocarbazole, or a salt thereof.

* * * * *